United States Patent [19]

Möller et al.

[11] Patent Number: 5,061,789

[45] Date of Patent: Oct. 29, 1991

[54] METHOD OF ISOLATING BLOOD-CLOTTING FACTOR IX

[75] Inventors: Wolfgang Möller, Oberursel; Michael Kraus, Leinfelden-Echterdingen, both of Fed. Rep. of Germany

[73] Assignee: Biotest Pharma GmbH, Dreieich, Fed. Rep. of Germany

[21] Appl. No.: 517,081

[22] Filed: May 1, 1990

[30] Foreign Application Priority Data

May 5, 1989 [DE] Fed. Rep. of Germany ....... 3914869

[51] Int. Cl.[5] .......................... C07K 3/02; C07K 3/20; C07K 3/22
[52] U.S. Cl. ................................... 530/381; 530/384; 530/416; 530/413
[58] Field of Search ............... 530/381, 384, 416, 413; 424/101

[56] References Cited

U.S. PATENT DOCUMENTS 3,920,625 11/1975 Anderson et al. .
4,721,572 1/1988 Jordan .
4,725,673 2/1988 Herring .

FOREIGN PATENT DOCUMENTS 0056629 5/1985 European Pat. Off. .
0041174 9/1985 European Pat. Off. .
2429191 1/1975 Fed. Rep. of Germany .
3826792 7/1989 Fed. Rep. of Germany .
8303760 11/1983 PCT Int'l Appl. .

OTHER PUBLICATIONS

Matsumoto et al., (1980), J. Biochem. 87, 535–540.
C. Michalski et al., "Large-Scale Production and Properties of a Solvent-Detergent...", Vox Sang 55 (1988) 4, pp. 202–210.
T. Burnouf et al., "Therapeutic Advantage of a High-Purity Factor IX...", Int. Symp. on Biotechnology of Plasma Proteins, Abstr. 4.09), (1988).

*Primary Examiner*—Garnette D. Draper
*Assistant Examiner*—R. K. Baker
*Attorney, Agent, or Firm*—Sprung Horn Kramer & Woods

[57] ABSTRACT

A method of isolating blood-clotting Factor IX. A solution containing the Factor IX is adsorbed onto an adsorbent carrying α-hydroxylamine groups, and the factor is eluted. The Factor IX from the eluate is adsorbed onto a matrix carrying sulfated carbohydrates, with the conductivity adjusted to 13–17 mS/cm, and eluted with a salt gradient. The pure Factor IX is concentrated and freeze-dried.

15 Claims, No Drawings

METHOD OF ISOLATING BLOOD-CLOTTING FACTOR IX

The invention concerns a simple method of isolating blood-clotting Factor IX in an almost pure form and at a high yield from plasma or other fractions by adsorbing the factor onto a matrix that carries α-hydroxylamine groups, eluting the factor, and adsorbing it onto a matrix that carries sulfated carbohydrates.

After hemophilia A, hemophilia B is the most common hereditary clotting disorder. The patients lack Factor IX, without which the blood cannot clot, and the condition can be treated by supplementing with preparations that contain it.

Hemophilia B is usually treated today with what are called PPSB concentrates, which contain in addition to Factor IX various levels of vitamin K dependent clotting Factors II, VII, and X. The specific activity of such preparations is, according to European Patents 56 629 and 41 174 for example, approximately 2.5U of Factor IX per milligram of protein.

One alternative to the PPSB concentrates for the treatment of clotting disorders are highly enriched Factor IX concentrates. Such concentrates, with a specific Factor IX activity of more than 10U per mg of protein can, however, be obtained at the current state of the art only from plasma by several fractionation steps. Examples are described in International Patent Application WO 83/03760 and in German OS 2 429 191.

German Patent 3 826 792 describes the isolation of a Factor IX concentrate with a specific activity of up to 20U per mg of protein with adsorbents carrying α-hydroxylamine groups.

An article by C. Michalski et al (Vox Sanguis 55 [1988], 4, 202-10) presents a method using both a DEAE anion exchange chromatography and heparin Sepharose that allows isolation of a Factor IX concentrate with a specific activity of approximately 10U per mg of protein.

An even higher purity of 120 to 150U of Factor IX per mg of protein was attained by T. Burnouf et al (Int. Symp. on Biotechnology of Plasma Proteins, Nancy, 5/17/1988, Abstr. 4.09) with two steps of anion-exchange chromatography and one of affinity chromatography. U.S. Pat. Nos. 3,920,625, 4,721,572, and 4,725,673 describe the purification of Factor IX concentrates with sulfated carbohydrates immobilized on organic and inorganic carriers. The affinity chromatography is usually the last step in a multistep purification method with a low yield in terms of the starting plasma, unless the final product also contains contaminants in the form of other proteins. Somewhat higher yields are often obtained by adding such protease inhibitors as benzamidine or PMSF. It is, however, advisable to avoid as much as possible adding foreign substances to plasma or to a final product that will be used to treat humans.

The object of the present invention is to provide a simple method of obtaining a Factor IX preparation that is as pure as possible, that has a specific activity higher than 150U of Factor IX per mg of protein, and that is almost free of other proteins.

This object is attained in accordance with the invention by treating plasma or other Factor IV containing fractions with a matrix that carries α-hydroxylamine groups and adsorbs Factor IX, rinsing the matrix with appropriate buffers, and specifically eluting the Factor IX. The Factor IX in the eluate is then attached to carriers with immobilized sulfated carbohydrates subject to conditions wherein almost no other proteins are adsorbed. The Factor IX is finally eluted with a salt gradient.

It has surprisingly been discovered that Factor IX can be obtained by way of this simple two-step method in a high yield and in an almost pure form. No non-physiological protease inhibitors had to be added to obtain the Factor IX clotting activity.

The starting material can be plasma, plasma fractions, or other solutions that contain Factor IX.

Plasma can for example be adsorbed in accordance with the invention at a slightly elevated conductivity, preferably 12 to 15 mS/cm, and at a pH of preferably 7.0 to 7.7 onto a α-hydroxylamine carrier, e.g. Fraktogel TSK-Amino (Merck, Darmstadt). The carrier is washed according to conditions such that the Factor IX is only inessentially eluted. This procedure is preferably carried out with low molecular-weight organic amines—1-amino-2-propanol, 1,3-diamino-2-propanol, or 1,3-diaminopropane for example—which are supposed to have a certain similarity to the α-hydroxylaminopropyl group, in a buffer with 10 mM citrate, 10 mM phosphate, and 100 mM sodium chloride at a pH of 7.5. The washing can also be carried out with the buffer and without amine, although the purity and yield would be somewhat lower. The Factor IX is then eluted from the carrier by increasing the concentration of amine or salt. Adding the low molecular-weight amine increases the specificity during the washing and while the Factor IX is being eluted.

The eluate with the Factor IX activity is then applied to a carrier with such sulfated carbohydrates as heparin Sephadex (Pharmacia, Freiburg), heparin Fraktogel TSK, heparin Eupergit (Röhm, Darmstadt), or dextran-sulfate Sepharose. The conductivity is adjusted to 13-17 and preferably to 15 mS/cm. Only Factor IX is accordingly extensively adsorbed onto the carrier and can then be eluted in an almost pure state with a salt gradient of 0 to 1M of sodium chloride for example. The accordingly obtained Factor IX eluate is concentrated by diafiltration and ultrafiltration and freeze-dried.

The yield from this simple procedure is up to 40% of the starting activity in the plasma for a Factor IX with a specific activity of 200 to 300U per mg of protein. The protein content of the fractions was determined by the micromethod of MM. Bradford (Anal. Biochem. 72 [1976], 248-54) or by the microkjeldahl method with a nitrogen detector in accordance with the instructions provided by the manufacturer (Antec Instruments Inc., Houston, Tex.).

Such specific activities have previously been obtainable only with multistep methods, and even then the yields were definitely below the 30–40% that can be obtained by the method in accordance with the invention.

Before or after the Factor IX is adsorbed onto the α-hydroxylamine or sulfated-carbohydrate matrix, the material can be sterilized with β-propiolactone and/or ultraviolet irradiation, with solvents or detergents, or by pasteurization with stabilizers to inactivate any human-pathogenic viruses.

The invention will now be described with reference to the following examples.

EXAMPLE 1

A 250 ml column with an α-hydroxylaminopropyl-carrying matrix, consisting of a copolymer of glycidyl methacrylate, pentaerythrol dimethacrylate, and polyvinyl alcohol, Fraktogel TSK-Amino (Merck, Darmstadt) for example, is equilibrated with 1500 ml of buffer A (10 mM of citrate, 10 mM of $Na_2HPO_4$, 100 mM of NaCl, pH 7.5).

5000 ml of plasma with a conductivity of 13 mS/cm are applied at a flow rate of 300 ml/h and washed with 1000 ml of buffer A. The Factor IX is eluted with a linear gradient of 0–0.5M of sodium chloride in buffer A. The fractions with a specific activity higher than 3U of Factor IX per mg of protein are pooled.

A 500 ml column with heparin Sepharose (Pharmacia, Freiburg) is equilibrated with 1000 ml of buffer A. The Factor IX eluate is diluted with buffer B (10 mM of citrate, pH 7.5) to a conductivity of 15 mS/cm and applied to the column. The column is washed with 500 ml of buffer B and eluted with a gradient of 0–1M NaCl in buffer B.

The Factor IX eluate is concentrated by diafiltration and ultrafiltration and freeze-dried. The overall yield of Factor IX was 30% of the starting activity in the plasma. The specific activity of the Factor IX was 270U of Factor IX per mg of protein.

EXAMPLE 2

1000 ml of citrate plasma are chromatographed as described in Example 1. The Factor IX is this time eluted from the α-hydroxylaminopropyl-matrix Fraktogel TSK-Amino with the free ligand, 1-amino-2-propanol. The column is washed with buffer A and with 0.2M of 1-amino-2-propanol in buffer A and eluted with 0.25M of 1-amino-2-propanol in buffer A.

The Factor IX eluate is chromatographed over heparin Sepharose as described in Example 1. The specific activity of the Factor IX was 265U of Factor IX per mg of protein. The yield was 39% of the starting activity in the plasma.

EXAMPLE 3

100 ml of plasma are chromatographed as described in Example 1. The heparin carrier is a copolymer of glycidyl methacrylate, pentaerythrol dimethacrylate, and polyvinyl alcohol (Fraktogel TSK, Merck, Darmstadt).

The heparin Fraktogel is prepared by reacting 50 g of Fraktogel TSK-Amino with 1.5 g of heparin and 150 mg of $NaCNBH_3$ in 50 ml of 0.2M phosphate buffer at a pH of 7.0 for 2 days at room temperature and washing it with distilled water.

The specific activity of the Factor IX was 200U per mg of protein and the yield was 27% in terms of the starting plasma.

EXAMPLE 4

1000 ml of plasma are chromatographed as described in Example 1. Dextran-sulfate Sepharose is employed instead of heparin Sepharose.

The dextran-sulfate Sepharose is prepared by reacting 100 ml of Sepharose 4B (Pharmacia, Freiburg) with 5 g of dextran sulfate in 100 ml of water and 4 g of cyanogen bromide at a pH of 11 for 10 minutes. The gel is allowed to stand 24 hours at a pH of 8 and washed with water and buffer.

The specific activity of the Factor IX was 210U per mg of protein at a yield of 31% in terms of the starting plasma.

EXAMPLE 5

1000 ml of plasma are allowed to stand overnight with 0.25% β-propiolactone at a pH of 8.0 and then irradiated with ultraviolet light. The cold-sterilized plasma is worked up as described in Example 2. At a yield of 20%, the purity was 210U per mg of protein.

EXAMPLE 6

1000 ml of citrate plasma are chromatographed as described in Example 2. Between the two chromatography steps, the eluate of the Fraktogel TSK-Amino is treated with 0.3% tri-N-butyl phosphate and 7% Tween 80 for 8 hours at 25° C. and irradiated with two 20-W ultraviolet lamps in a rotational-flow apparatus at 600 rpm and at a rate of 20 l per hour at a 1-cm distance.

The specific activity of the Factor IX was 245U of Factor IX per mg of protein. The yield was 35% of the starting activity in the plasma.

EXAMPLE 7

100 ml of a commercial PPSB with a specific activity of 0.6U of Factor IX per mg of protein are chromatographed as described in Example 2 over 30 ml of each of the adsorbents employed in Example 1. It was possible in this way to isolate a Factor IX with 210U per mg of protein at a yield of 76%.

It will be understood that the specification and examples are illustrative but not limitative of the present invention and that other embodiments within the spirit and scope of the invention will suggest themselves to those skilled in the art.

What is claimed is:

1. A method of isolating blood-clotting Factor IX, comprising
    a) contacting a solution containing Factor IX with an adsorbent carrying α-hydroxylaminopropyl groups, thereby to absorb the Factor IX, and then eluting the Factor IX to product an eluate,
    b) adjusting the conductivity of the eluate of step (a) to 13–17 mS/cm, and
    c) contacting the solution of Factor IX from the adjusted eluate of step (b) with a matrix carrying sulfated carbohydrates selected from the group consisting of (i) heparin immobilized on a copolymer of glycidyl methacrylate, pentaerythrol dimethacrylate, and polyvinyl alcohol, (ii) heparin immobilized on a copolymer of methacrylamide, N-methylene-bis-methacrylamide and allylglycidyl ether, (iii) heparin immobilized on a carbohydrate polymer, and (iv) dextran sulfate immobilized on a carbohydrate polymer, and eluting the Factor IX from the matrix with a salt gradient to produce a second eluate.

2. A method according to clam 1, including the further step (d) of concentrating and freeze drying the Factor IX eluate of step (c).

3. The method according to claim 1, wherein the α-hydroxylaminopropyl carrier is a copolymer of glycidyl methacrylate, pentaerythrol dimethacrylate, and polyvinyl alcohol.

4. The method according to claim 1, wherein in step (a) the eluant for the Factor IX from the α-hydroxylpropylamino carrier is a low molecular-weight primary organic amine.

5. The method according to claim 4, wherein the eluant is 1-amino-2-propanol.

6. The method according to claim 4, wherein the eluant is 1,3-diamino-2-propanol or 1,3-diamino-propane.

7. The method according to claim 1, wherein in step (a) the adsorption onto the α-hydroxylpropylamino carrier is carried out as column chromatography, batch by batch, or on membranes.

8. The method according to claim 1, wherein in step (c) the matrix that carries the sulfated carbohydrate is heparin immobilized on a copolymer of glycidyl methacrylate, pentaerythrol dimethacrylate, and polyvinyl alcohol.

9. The method according to claim 1, wherein in step (b) the matrix that carries the sulfated carbohydrate is heparin immobilized on a copolymer of methacrylamide, N-methylene-bis-methacrylamide, and allylglycidyl ether.

10. The method according to claim 1, wherein in step (b) the matrix that carries the sulfated carbohydrate is heparin immobilized on a carbohydrate polymer.

11. The method according to claim 1, wherein in step (b) the matrix that carries the sulfated carbohydrate is dextran sulfate immobilized on a carbohydrate polymer.

12. The method according to claim 1, wherein in step (b) the contact of the solution with the matrix that carries the sulfated carbohydrate is carried out as column chromatography, batch by batch, or on membranes.

13. A method according to claim 1, wherein the starting solution is a plasma that contains the Factor IX or a plasma fraction.

14. The method according to claim 1, including the additional step of inactivating any viruses in the solution either before or after each of steps (a) and (b).

15. The method according to claim 14, wherein the virus inactivation is effected by treatment with at least one of β-propiolactone, ultraviolet irradiation, a solvent or detergent, and pasteurization with a stabilizer in solution.

* * * * *

UNITED STATES PATENT AND TRADEMARK OFFICE
CERTIFICATE OF CORRECTION

PATENT NO. : 5,061,789

DATED : October 29, 1991

INVENTOR(S) : Moller et al.

It is certified that error appears in the above-identified patent and that said Letters Patent is hereby corrected as shown below:

| | | |
|---|---|---|
| Title Page | Item | [75] Inventors: After " Echterdingen " insert 3rd Inventor -- Bertram Eichentopf, Bad Soden, --, delete "both " and substitute -- all -- |
| Col. 4, claim 4 lines 2-3 | | Delete " $\alpha$-hydroxylpropylamino " and substitute -- $\alpha$-hydroxylaminopropyl -- |
| Col. 5, claim 7 line 2 | | Delete " $\alpha$-hydroxylpropylamino " and substitute -- $\alpha$-hydroxylaminopropyl -- |
| Col. 5, claim 9 line 2 | | Delete " (b) " and substitute -- (c) -- |
| Col. 6, claims 10, 11 & 12, line 2 | | Delete " (b) " and substitute (c) -- |
| Col. 6, line 17, "(b)" should read --(c)--. | | |

Signed and Sealed this

Seventeenth Day of August, 1993

*Attest:*

BRUCE LEHMAN

*Attesting Officer*     *Commissioner of Patents and Trademarks*